United States Patent
Sakulowski

(10) Patent No.: US 12,302,899 B2
(45) Date of Patent: *May 20, 2025

(54) LIQUID CONCENTRATE FOR PRESERVATION

(71) Applicant: ASHLAND INDUSTRIES EUROPE GMBH, Schaffhausen (CH)

(72) Inventor: Stefan Sakulowski, Norderstedt (DE)

(73) Assignee: ISP Investments LLC, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/189,298

(22) Filed: Mar. 24, 2023

(65) Prior Publication Data

US 2023/0225318 A1    Jul. 20, 2023

Related U.S. Application Data

(63) Continuation of application No. 16/755,653, filed as application No. PCT/EP2018/078543 on Oct. 18, 2018, now Pat. No. 11,638,426.

(30) Foreign Application Priority Data

Oct. 18, 2017    (EP) .................................... 17197082

(51) Int. Cl.
| | | |
|---|---|---|
| A01N 37/10 | (2006.01) | |
| A01N 25/04 | (2006.01) | |
| A01N 25/34 | (2006.01) | |
| A01N 31/02 | (2006.01) | |
| A61K 8/34 | (2006.01) | |

(52) U.S. Cl.
CPC ............. A01N 37/10 (2013.01); A01N 25/04 (2013.01); A01N 25/34 (2013.01); A01N 31/02 (2013.01); A61K 8/34 (2013.01)

(58) Field of Classification Search
CPC ......... A01N 25/04; A01N 37/10; A61K 8/368
See application file for complete search history.

(56) References Cited

U.S. PATENT DOCUMENTS

| | | | |
|---|---|---|---|
| 5,965,115 A | 10/1999 | Bolich, Jr. et al. | |
| 8,501,206 B2 | 8/2013 | Beilfuss et al. | |
| 9,883,671 B2 * | 2/2018 | Gradtke ................. | A01N 31/04 |
| 2004/0151742 A1 | 8/2004 | Beilfuss et al. | |
| 2018/0092357 A1 | 4/2018 | Premachandran et al. | |

FOREIGN PATENT DOCUMENTS

| | | |
|---|---|---|
| DE | 1026756 A1 | 2/1992 |
| DE | 19922538 A1 | 11/2000 |
| DE | 10122380 A1 | 11/2002 |
| EP | 2 873 321 A1 | 5/2015 |
| WO | 2012/151441 A1 | 11/2012 |
| WO | 2013/067150 A2 | 5/2013 |
| WO | 2018/033406 A1 | 2/2018 |

OTHER PUBLICATIONS

Dielectric Constants, https://macro.lsu.edu/howto/solvents/Dielectric%20Constant%20.htm, 2 pages.*
"Technical Data Sheet—Verstatil BOB," Supplier—Dr. Straetmans GmbH, dated Mar. 27, 2014, Retrieved from the Internet URL: http://www.quidelta.com.mx/archivos/TDS_VERSATILBOB.pdf2016-06-03_10_51_14_SyP_hoja_en.pdf, p. 1-3.
"Technical Data Sheet—Verstatil TBO," Supplier—Dr. Straetmans GmbH, dated Jan. 16, 2015, Retrieved from the Internet URL: http://www.quidelta.com.mx/archivos/TDS Versatil TBO-ENG.pdf2016-05-31_16_40_06_SyP_hoja_en.pdf, p. 1-3.
Woodruff, J., "Cosmetic Preservation," date Jan. 1, 2014, Retrieved from the Internet URL: http://creativedevelopments.co.uk/wp-content/uploads/2013/10/Cosmetic-Preservation-2014.pdf, p. 1-6.
International Search Report of the International Searching Authority for PCT/EP2018/078543 with mailing date of Nov. 19, 2018.
Office Action issued in European Patent Application No. 17 197 082.5 dated Apr. 7, 2021.
"Final Report on the Safety Assessment of Benzyl Alcohol, Benzoic Acid, and Sodium Benzoate," International Journal of Toxicology, vol. 20, No. Supplement 3, Jan. 1, 2001, pp. 23-50, XP009058688.
Johnson et al., "Safety Assessment of 1,2-Glycols as Used in Cosmetics," International Journal of Toxicology, vol. 31, No. Supplement 2, Jan. 1, 2012, pp. 147S-168S, XP055789908.
Fiume et al., "Safety Assessment of Propylene Glycol, Ttripropylene Gglycol, and PPGs as Used in Cosmetics," International Journal of Toxicology, vol. 31, No. Supplement 2, Sep. 1, 2012, pp. 245S-260S, XP055790019.
Kinnunen et al., "Antibacterial and Antifungal Properties of Propylene Glycol, Hexylene Glycol, and 1,3-Butylene Glycol In vitro," Acta Derm Venereol (Stockh), vol. 71, No. 2, Jan. 1, 1991, pp. 148-150, XP000670892.
U.S. Appl. No. 16/755,653, filed Apr. 13, 2020.

* cited by examiner

*Primary Examiner* — Kyle A Purdy
(74) *Attorney, Agent, or Firm* — William J. Davis; Nathalie Tietcheu

(57) ABSTRACT

The invention relates to a composition, which comprises: a)—From 15 weight % to 25 weight % of 1,2-octanediol, b)—From 15 weight % to 25 weight % of benzoic acid, c)—From 50 weight % to 70 weight % of propylene glycol, wherein the content of aromatic alcohol is less or equal to 5 weight % relative to the weight of the liquid concentrate; its use of a composition, for the preservation of cosmetics products, household products or technical products.

10 Claims, No Drawings

LIQUID CONCENTRATE FOR PRESERVATION

CROSS REFERENCE TO RELATED APPLICATIONS

This application is a Continuation of application Ser. No. 16/755,653, filed on Apr. 13, 2020, which is the National Phase under 35 U.S.C. § 371 of International Application No. PCT/EP2018/078543, filed on Oct. 18, 2018, which claims the benefit under 35 U.S.C. § 119(a) to Patent Application No. 17197082.5, filed in Europe on Oct. 18, 2017, all of which are hereby expressly incorporated by reference into the present application.

The invention relates to an antimicrobial liquid concentrate and the use of said liquid concentrate for preservation, particularly of cosmetic products, i.e. wet wipes.

Preservatives based on carboxylic acids such as benzoic acid, sorbic acid, dehydroacetic acid, undecylenic acid, or salts thereof are known. Although such acids and salts are toxicologically safe, they are not sufficiently effective when used alone. The cosmetic industry therefore continues to seek improved preservatives based on organic acids.

DE 19922538 A1 describes a liquid concentrate comprising carboxylic acids, aromatic alcohols, and solvents, wherein the total content these components is greater than 45 wt. %. However, the use of aromatic alcohols in preservatives for cosmetics is increasingly being criticized.

DE 4026756 A1 discloses a preservative comprising from 5 wt. % to 60 weight % (wt. %) of an organic acid selected from benzoic acid, 4-hydroxy benzoic acid, salicylic acid, formic acid, acetic acid, propionic acid, sorbic acid, undecylenic acid, and/or dehydroacetic acid and salts thereof; from 10 wt. % to 95 wt. % of aromatic alcohols, and from 0.1 wt. % to 20 wt. % of poly(hexamethylenebiguanide) salts; optionally 0.1 wt. % to 20 wt. % of substituted glycerol ethers and/or solvents such as water, glycols such as propyleneglycol, dipropyleneglycol, and triethyleneglycol, or glycol ethers such as butyl diglycol, in order to improve low-temperature stability.

Another known product is euxyl® K 702, produced by Schülke & Mayr GmbH (Norderstedt, Federal Republic of Germany), which comprises benzoic acid, poly(hexamethylene biguanide) hydrochloride, dehydroacetic acid, and phenoxyethanol. However, the use of cationic surfactants (such as poly(hexamethylene biguanide) salts), particularly in large amounts such as 1 wt. %, in anionic surfactant-based products such as shampoos is problematic, because this can result in interactions causing the formation of precipitates or deactivation. In addition, according to EU Regulation 944/2013, poly(hexamethylene biguanide) salts have been classified since 2015 as classified as a carcinogenic, mutagenic or toxic for reproduction substance (CMR2 substance), and its use was in the past prohibited in cosmetics products. Although currently allowed again, market acceptance is doubtful.

DE 10122380 A1 discloses an alcohol-free liquid concentrate, for example for the preservation of cosmetics, which comprises a carboxylic acid component (A), a stabilizer component (B), and solvents (C). The carboxylic acid component (A) comprises at least one salt of benzoic acid, propionic acid, salicylic acid, sorbic acid, 4-hydroxy benzoic acid, dehydroacetic acid, or 10-undecylenic acid, and optionally one or a plurality of the above-mentioned free acids. Illustrative concentrates described in said document in addition contain up to approximately 45 wt. % of a mixture of sodium benzoate with potassium sorbate, formaldehyde or a formaldehyde depot compound (such as dimethylol dimethyl hydantoin). However, there is increasing criticism of cosmetic preservatives containing formaldehyde or formaldehyde depot compounds.

WO 201 2/1 51 441 A1 describes antimicrobial formulations which comprises a fatty acid and at least one natural product or product of natural origin, such as 1,3-pro-panediol or an alcohol-containing solvent, or an organic acid or salt thereof such as potassium sorbate or benzoic acid. WO 201 2/1 51 441 A1 for example discloses an anhydrous mixture comprising approximately 80 wt. % 1,3-propanediol, 10 wt. % (ethylhexyl) glycerol, and 10 wt. % potassium sorbate. The preservatives according to this document are used in skin care products such as shampoos, lotions, conditioners and soaps. However, it has been found, that compositions containing e.g. potassium sorbate and sodium benzoate cannot be formulated as clear solutions, if the content of sorbate and benzoate is too high and/or the content of 1,3-propanediol is two. Although 1,3-propanediol alone is readily soluble in water, it is not possible to prepare a clear solution from 45 wt. % of water, 15 wt. % of potassium sorbate, and 30 wt. % of sodium benzoate with 10 wt. % of 1,3-propanediol. Moreover, the formulations according to WO2012/151441 A1 act as thickeners, which is a drawback in use for the preservation of wet wipes.

PCT/EP2017/069722 filed on 3 Aug. 2017 discloses an aqueous antimicrobial liquid concentrate, which comprises from 5 wt. % to 20 wt. % of one or a plurality of diols selected from alkanediols having from six to twenty carbon atoms, and monoalkyl glycerol ethers having from four to eighteen carbon atoms, from 20 wt. % to 60 wt. % of one or a plurality of salts of one or a plurality of organic acids selected from the group composed of sorbic acid, benzoic acid, anisic acid, salicylic acid, 4-hydroxy benzoic acid, cinnamic acid, succinic acid, and levulinic acid, and optionally one or a plurality of the above-mentioned free acids, and from 30 wt. % to 70 wt. % of water, wherein the content of aromatic alcohol is a maximum of 5 wt. % relative to the weight of the liquid concentrate; and its use, for the preservation of cosmetic products, household products, and technical products. However, as water is essential for microbiological growth, the potential of microbiological contamination in the final cosmetic product increases.

Compositions of organic acids and aromatic alcohols are already known in the form of a concentrate. Aromatic alcohols are in public discussion because of the possible potential of sensitisation. Therefore, there is a need of microbiologically active compositions which do not comprise any aromatic alcohols. additional combination partners must fulfil the criteria of cosmetic ingredients. They must be storage stable, soluble, processable and result in a clear composition in the final concentrate. Water-free cosmetic products require water-free preservation to avoid an additional amount of water which offers condition for microbiological growth. Therefore, the composition must have antimicrobial activity and good compliance properties, combined with use in low-water of water-free systems.

Accordingly, the present invention aims to provide preservatives as concentrates, that can easily be formulated into clear solutions, even in an aqueous dilution.

Moreover, the preservative should have little or no effect on the properties of the final product and therefore need not necessarily contain surfactants, emulsifiers, solvents or aromatic alcohols.

In a first aspect, the invention therefore relates to a composition, which comprises:

a)—From 15 weight % to 25 weight % of 1,2-octanediol,
b)—From 15 weight % to 25 weight % of benzoic acid,
c)—From 50 weight % to 70 weight % of propylene glycol, wherein the content of aromatic alcohol is less or equal to 5 weight % relative to the weight of the liquid concentrate.

According to a particular embodiment, the composition as hereinbefore defined, is free from aromatic alcohol.

In the context of the invention, aromatic alcohols mainly mean alcohols, such as phenoxyethanol, phenoxypropanol, phenethyl alcohol, phenyl propanol and benzylic alcohol, and which are commonly used in the formulation of cosmetics products, household products or technical products.

According to another particular embodiment, the composition as hereinbefore defined, is free from water.

According to another particular embodiment, the invention relates to a composition as hereinbefore defined, wherein the weight ratio 1,2-octanediol/benzoic acid is equal to 1.

According to other particular embodiments, the invention relates to a composition as hereinbefore defined, wherein the weight ratio 1,2-octanediol/propylene glycol is greater or equal to 0.2 and less or equal to 0.5; and/or to a composition as hereinbefore defined, wherein the weight ratio benzoic acid/propylene glycol is greater or equal to 0.2 and less or equal to 0.5.

According to a more specific embodiment, the invention relates to a composition as hereinbefore defined, which consists in, for 100% of its weight:
a)—From 15 weight % to 25 weight % of 1,2-octanediol,
b)—From 15 weight % to 25 weight % of benzoic acid, and
c)—From 50 weight % to 70 weight % of propylene glycol.

According to a very specific embodiment of this more specific embodiment, the composition as hereinbefore defined, is characterized by a weight ratio 1,2-octane-diol/benzoic acid equal to 1; and said composition more specifically consists in, for 100% of its weight:
a)—20 weight % of 1,2-octanediol,
b)—20 weight % of benzoic acid, and
c)—60 weight % of propylene glycol.

The invention also relates to the use of a composition as hereinbefore defined, for the preservation of cosmetics products, household products or technical products and/or as a disinfectant.

According to a preferred embodiment, the invention relates to the use of a composition as hereinbefore defined for the preservation of wet wipes.

The invention also relates to a method to preserve cosmetics products, household products or technical products, characterized in that an efficient amount of a composition as hereinbefore defined, is added in the mixture of the constituents of said cosmetics products, household products or technical products, during the preparation of said cosmetics products, household products or technical products, such as a wet wipe.

In the context of the invention, an efficient amount approximatively means a weight proportion of approximately from 0.05 wt. % to 3% wt. % of said cosmetics products, household products or technical products.

Germ Count Reduction Test

The following concentrates were produced (composition given in wt. %, Table 1 a):

TABLE 1a

| Composition | I | II | III |
|---|---|---|---|
| Benzoic acid | 20.00 | 0.00 | 20.00 |
| 1,2-octanediol | 0.00 | 20.00 | 20.00 |
| Propyleneglycol | 80.00 | 80.00 | 60.00 |

The following organisms were tested:

TABLE 1b

| Species | |
|---|---|
| Staphylococcus aureus | ATCC no 6538 |
| Escherichia coli | ATCC no11229 |
| Pseudomonas aeruginosa | ATCC no 15442 |

Dilutions of the concentrates are prepared at a concentration of 1 wt. %, in demineralized water and and adjusted to pH=5.0 for *Staphylococcus aureus* and *Escherichia coli* and to pH=5.5 for *Pseudomonas aeruginosa*.

24-hour CASO (casein peptone-soybean flour peptone solution) cultures are prepared from 24-hour tryptone-soy agar (TSA) cultures of *Staphylococcus aureus, Escherichia coli* and *Pseudomonas aeruginosa*. Incubation takes place at 30° C. (TSA) and (CASO) 37° C.

25 cm$^3$ of the end solutions are each inoculated with 0.1 cm$^3$ of microorganism suspensions (initial microorganism count: approximatively 10$^9$cfu/ml).

The solutions are streaked out onto TSA after 3, 6, 24 and 48 hours. The cultures are incubated for 48 hours at 37° C.

The evaluation of the microbioloical growth of the streaks is made semi-quantitatively.

The results are found in the following table 1c

TABLE 1c

| Test microorganism | | 3 h | 6 h | 24 h | 48 h |
|---|---|---|---|---|---|
| Staphylococcus aureus | Water | C | C | C | C |
| | I | C | C | C | C |
| | II | ++++ | +++ | ++ | + |
| | III | ++++ | ++++ | − | − |
| Escherichia coli | Water | C | C | C | C |
| | I | C | C | C | C |
| | II | C | +++ | − | − |
| | III | ++++ | + | − | − |
| Pseudomonas aeruginosa | Water | C | C | C | C |
| | I | C | C | C | C |
| | II | C | C | C | C |
| | III | ++++ | + | − | − |

| Symbol | Finding | Germ count/ml |
|---|---|---|
| − | No growth | <100 |
| + | Slight growth | Around 10$^2$ |
| ++ | Moderate growth | Around 10$^3$ |
| +++ | Heavy growth | Around 10$^4$ |
| ++++ | Massive growth | Around 10$^5$ |
| C | Surface covered | Around 10$^6$ |

The experimental results show that the combination of benzoic acid and 1,2-octanediol in propylene glycol, exhibits an antimicrobial activity with a faster efficacy than benzoic acid alone or 1,2-octanediol alone in the same solvent. The use of propyleneglycol as a solvent provides the usability in water-free systems. This concentrate is a clear solution that is user compliant and also storage-stable.

The invention claimed is:
1. A liquid concentrate consisting of: a) from 15 weight % to 25 weight % of 1,2-octanediol; b) from 15 weight % to 25 weight % of benzoic acid; and c) from 50 weight % to 70 weight % of propylene glycol; wherein a content of aromatic alcohol is less or equal to 5 weight % relative to the weight of the liquid concentrate.

2. The liquid concentrate according to claim 1, which is free from aromatic alcohol.

3. The liquid concentrate according to claim 1, which is free from water.

4. The liquid concentrate according to claim 1, wherein the weight ratio 1,2-octanediol/benzoic acid is equal to 1.

5. The liquid concentrate according to claim 1, wherein the weight ratio benzoic acid/propylene glycol is greater or equal to 0.2 and less or equal to 0.5.

6. The liquid concentrate according to claim 1, wherein the weight ratio 1,2-octane-diol/benzoic acid is equal to 1.

7. The liquid concentrate according to claim 1, consisting of: a) 20 weight % of 1,2-octanediol; b) 20 weight % of benzoic acid; and c) 60 weight % of propylene glycol.

8. A method of using the liquid concentrate according to claim 1 as a disinfectant or preservative, the method comprising adding an efficient amount of the liquid concentrate to cosmetics products, household products, or technical products for the purpose of disinfecting or preserving the cosmetics products, household products, or technical products.

9. The method of claim 8 wherein the liquid concentrate is added to wet wipes for the preservation of the wet wipes.

10. The method of claim 8 wherein the composition is added to the cosmetics products, household products, or technical products during the preparation of the cosmetics products, household products, or technical products.

* * * * *